United States Patent
Roth

(10) Patent No.: US 6,524,000 B1
(45) Date of Patent: Feb. 25, 2003

(54) TIME-TEMPERATURE INDICATORS ACTIVATED WITH DIRECT THERMAL PRINTING AND METHODS FOR THEIR PRODUCTION

(75) Inventor: Joseph D. Roth, Springboro, OH (US)

(73) Assignee: NCR Corporation, Dayton, OH (US)

( * ) Notice: Subject to any disclaimer, the term of this patent is extended or adjusted under 35 U.S.C. 154(b) by 0 days.

(21) Appl. No.: 09/302,482

(22) Filed: Apr. 30, 1999

(51) Int. Cl.$^7$ .......................... B41J 31/06; B41M 7/00; G01N 31/22
(52) U.S. Cl. ................. 374/102; 374/104; 374/106; 116/206; 347/221; 503/201
(58) Field of Search .................. 374/102, 104, 374/106; 116/206; 347/221, 171; 503/201

(56) References Cited

U.S. PATENT DOCUMENTS

| | | | |
|---|---|---|---|
| 3,080,254 A | 3/1963 | Grant, Jr. | |
| 3,094,417 A | 6/1963 | Workman | |
| 3,241,997 A | 3/1966 | Schutzner | |
| 3,795,532 A | 3/1974 | Newman et al. | |
| 3,857,821 A | * 12/1974 | Becker et al. | 526/285 |
| 3,942,467 A | 3/1976 | Witonsky | |
| 3,999,946 A | * 12/1976 | Patel et al. | 374/102 |
| 4,082,901 A | 4/1978 | Laridon et al. | |
| 4,189,399 A | 2/1980 | Patel | |
| 4,208,186 A | 6/1980 | Patel | |
| 4,212,153 A | 7/1980 | Kydonieus et al. | |
| 4,220,747 A | 9/1980 | Preziosi et al. | |
| 4,228,126 A | * 10/1980 | Patel | 374/102 |
| 4,235,108 A | * 11/1980 | Patel | 374/102 |
| 4,238,352 A | * 12/1980 | Patel | 374/102 |
| 4,276,190 A | * 6/1981 | Patel | 374/102 |
| 4,298,348 A | * 11/1981 | Ivory | 116/206 |
| 4,339,240 A | * 7/1982 | Patel | 374/106 |
| 4,389,217 A | 6/1983 | Baughman et al. | |
| 4,533,640 A | 8/1985 | Shafer | |
| 4,737,463 A | * 4/1988 | Bhattacharjee et al. | 374/102 |
| 4,812,053 A | * 3/1989 | Bhattacharjee | 374/102 |
| 4,917,503 A | * 4/1990 | Bhattacharjee | 374/102 |
| 4,931,420 A | 6/1990 | Asano et al. | |
| 5,047,455 A | * 9/1991 | Hesse et al. | 523/508 |
| 5,057,434 A | * 10/1991 | Prusik et al. | 116/206 |
| 5,672,465 A | 9/1997 | Patel et al. | |

FOREIGN PATENT DOCUMENTS

| | | | |
|---|---|---|---|
| EP | 1048476 A1 | * 11/2000 | 347/221 |
| EP | 1048477 A1 | * 11/2000 | 347/221 |

OTHER PUBLICATIONS

*Handbook of Imaging Materials*, 1991, ed. by Arthur S. Diamond (Marcel Dekker, New York), Subsection 11.3.
*Imaging Systems*, 1976, Kurt I. Jacobson and Ralph E. Jacobson (The Focal Press, London and New York), in Chapter VII, subsection 7.1 on Thermography.

* cited by examiner

*Primary Examiner*—David Martin
*Assistant Examiner*—Jeanne-Marguerite Goodwin
(74) *Attorney, Agent, or Firm*—Richard J. Traverso

(57) ABSTRACT

Recording materials are converted in a direct thermal imaging apparatus to time temperature indicators by exposure to heat from the thermal print head of a direct thermal printer. Methods for converting a recording material to a time temperature indicator comprise heating the recording material with a direct thermal imaging apparatus. The recording material contains an indicator compound which is convertible from an inactive state to an active state when heat is applied thereto by a direct thermal imaging apparatus for less than one second. Time-temperature indicators with active indicator compounds in a printed pattern are formed by a direct thermal imaging apparatus.

26 Claims, 1 Drawing Sheet

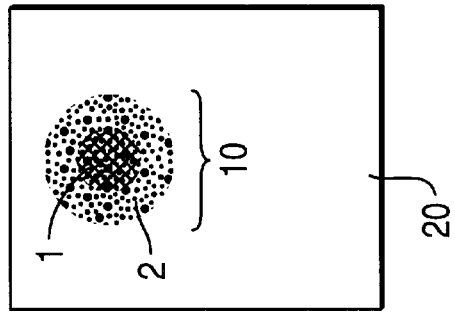
FIG. 1A  FIG. 1B
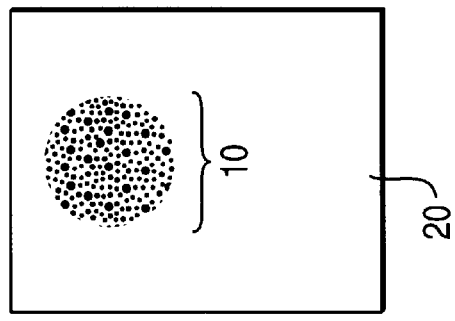
FIG. 1C  FIG. 1D
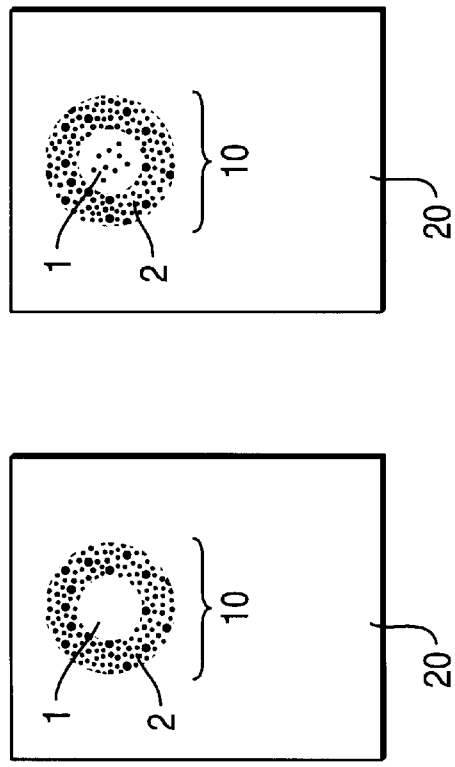

TIME-TEMPERATURE INDICATORS ACTIVATED WITH DIRECT THERMAL PRINTING AND METHODS FOR THEIR PRODUCTION

BACKGROUND OF THE INVENTION

The invention relates to the field of time-temperature indicators (TTIs). TTIs are colorimetric labels which respond to cumulative exposure to time and temperature. TTIs provide a visual indicator that gradually changes with time, typically faster at elevated temperatures and slower at colder temperatures.

TTIs are attached to perishable products at the time of production to monitor the cumulative time/temperature exposure. TTIs are used for monitoring time and temperature exposure of a wide variety of items including perishables in-transit, consumer packages, and medical perishables. TTIs are typically more reliable in monitoring the remaining shelf life of a perishable product than expiration dates such as "sell-by" or "use-by" dates. Expiration dates assume a certain temperature history, and temperature histories that vary from this assumption result in either the sale of a spoiled product or the premature disposal of a good product. In contrast, TTIs respond directly to temperature and reflect the temperature history of the product.

TTIs are commonly attached to shipping boxes for use by commercial distributors in the distribution of food and pharmaceuticals. The most common use is to ensure the integrity of the cold chain up to the supermarket.

Prepared TTIs have the disadvantage in that they must be stored at low temperatures or protected from actinic radiation prior to use. This requirement greatly increases the cost of production of TTIs and introduces an element of uncertainty as to the reliability of the indicators. Therefore, there is a need for TTI labels that can be activated at the site of application, thereby obviating a need for protection of the labels prior to use.

SUMMARY OF THE INVENTION

In accordance with this invention, there is provided a recording material which is suitable for use in a direct thermal imaging apparatus and which contains at least one indicator compound that is convertible from an inactive state to an active state by the application of heat within a direct thermal imaging apparatus. The terms "Time-temperature indicator" and "TTI",as used herein, refer to any colorimetric label which responds to an exposure element in a manner that indicates the degree of exposure to that element. Exposure elements include, for example, time, air, visible light, temperature, actinic radiation, and atomic radiation.

The recording material is processed in the direct thermal imaging apparatus by the generation of sufficient heat to convert the indicator compound from an inactive state to an active state to form a functional TTI. Once in the active state, indicator compounds serve to monitor the exposure of the TTI to various exposure elements. Also in accordance with this invention, a method of generating a time-temperature indicator (TTI) is disclosed which entails providing a recording material suitable for use in a direct thermal imaging apparatus, wherein the recording material contains at least one indicator compound. The method also entails heating the recording material in the direct thermal imaging apparatus to convert the indicator compound from an inactive state to an active state to form a functional TTI. Once in the active state, indicator compounds serve to monitor the exposure of the TTI to various exposure elements.

A recording material containing an inactive form of an indicator compound can be manufactured, stored and shipped under normal conditions without resort to refrigerated and light-protected environments. The indicator compound can then be activated when desired through processing in a direct thermal imaging apparatus.

Indicator Compounds

Indicator compounds that are contemplated as part of this invention are any compounds which exhibit detectable changes in response to an exposure element, wherein the compounds may be converted from an inactive state to an active state through the application of heat by a direct thermal imaging apparatus. Preferred compounds are kinetic indicator compounds which provide a change in color (typically darken) from a chemical reaction in response to the exposure elements of interest such as the integrated time and temperature. The use of kinetic indicator compounds which respond to air, actinic radiation or atomic radiation and the TTIs prepared therewith, are also contemplated as part of this invention.

A preferred temperature range for integrated TTIs responding to both time and temperature, or for TTIs which respond primarily to temperature will depend on their intended use. Where the TTI is to detect thawing, a range from about 0° C. and above is preferred. Where the TTI is to detect freezing, a range of about 0° C. and below is preferred. Manipulation of the response to different temperatures can be accomplished through the selection of indicator compounds and additives known in the art.

Preferred wavelength and intensity ranges for TTIs which respond primarily to actinic radiation will also depend on the intended use of the TTI. For example, where the TTI is intended to detect the exposure of film to harmful radiation, the TTI may be responsive to x-rays, UV light and visible light. Manipulation of the response to radiation at different wavelengths and intensities can be accomplished through the selection of indicator compounds and additives known in the art.

It is contemplated that activation of indicator compounds by processing in a thermal imaging apparatus may occur by various mechanisms including, for example, the following: melt recrystallization of the compounds to transform inactive compounds into active compounds, the application of heat to combine more than one indicator compound wherein the combination of the indicator compounds results in the activation of the compounds, the activation of an initiator compound which catalyzes the polymerization of the indicator compounds. A preferred method of activation is by melt recrystallization. As another example, two different indicator compounds may be present in encapsulated form within the recording material; wherein the compounds are able to mix and polymerize only after the application of heat has released the encapsulated forms. As a further example, substantially inactive compounds may be converted to substantially active compounds through heat activation of an initiator compound. For example, peroxides which thermally decompose into free radicals may be employed as an initiator compound to convert substantially inactive compounds into substantially active compounds.

Preferred temperature ranges for conversion of the indicator compounds from the inactive state to the active include those typically applied to a recording material with conventional thermal printers. The operating temperature of commercially available thermal printers varies widely, typically within the range from 50° C. to 250° C.

Particularly preferred compounds that are contemplated as part of this invention are acetylenic compounds having at least two conjugated acetylene groups (—C≡C—C≡C—) per molecule. The manufacture and use of acetylenic compounds as time-temperature indicators are described in the following U.S. Patents, all of which are hereby incorporated by reference: U.S. Pat. No. 3,999,946 (Patel et al.); U.S. Pat. No. 4,220,747 (Preziosi et al.); U.S. Pat. No. 4,189,399 (Patel); U.S. Pat. No. 4,228,126 (Patel et al.); U.S. Pat. No. 4,208,186 (Patel); U.S. Pat. No. 4,235,108 (Patel); U.S. Pat. No. 4,276,190 (Patel); U.S. Pat. No. 4,298,348 (Ivory); U.S. Pat. No. 4,339,240 (Patel); U.S. Pat. No. 4,238,352 (Patel); U.S. Pat. No. 4,389,217 (Baughman et al.); U.S. Pat. No. 4,737,463 (Bhattachajee et al.).

As described in U.S. Pat. Nos. 4,228,126 and 4,298,348, an inactive form of a diacetylene can exist at ambient temperature and ambient light conditions for indefinitely long periods of time. The inactive form can be subjected to gamma radiation at room temperature or thermal annealing below its melting point, without being converted to an active form. The inactive form can be converted by melt recrystallization into an active form, which can undergo 1,4-addition polymerization that results in a brightly colored polymer.

Several crystalline inactive and crystalline active forms of a diacetylene compound, of the same chemical composition, may exist. In such cases these inactive and active forms will exhibit the same general properties for "the active form" and "the inactive form",respectively, as described herein, and are included within the scope of this invention.

Diacetylene compounds, which are applicable in the invention, are also adequately described in U.S. Pat. No. 3,999,946. Generally, cyclic or acyclic diacetylenes, containing at least two conjugated —C≡C— groups are applicable in the invention including symmetrically or unsymmetrically substituted diynes, triynes, tetraynes and hexaynes. In addition, mixtures of diacetylenes or co-crystallized compositions of diacetylenes, as described in U.S. Pat. No. 4,189,399, can be employed. In the simplest case, diacetylenes are of the form R—C≡C—C≡C—R', where R or R' can be the same or different substituent groups. Examples of R or R' groups include alkyl, aryl, benzoate, sulfonate, urethane, acid, alcohol, and carbazolyl. Preferred derivatives include mono and bisulfonates, mono and bisurethanes, mono and bisacids, mono and bisalcohols, and mono and bis carbazolyl derivatives of acetylenic compounds. Such preferred compounds, and derivatives thereof, are most useful as integrated time-temperature history indicators or integrated radiation-dosage history indicators over the time and temperatures likely to be experienced by commercial, perishable products. Examples of acetylenic compounds useful as indicators in this invention include the following:

2,4-hexadiyn-1,6-diol bis(phenylurethane) (HDDPU)

2,4-hexadiyn-1,6-diol bis(p-methoxybenzene sulfonate) (PMOBS)

9-(N-carbazolyl)-5,7-nonadiyn-1-ol phenylurethane (PUCNDO)

o,o'-diacetylenyldiphenyl glutarate (DADPG)

2,4-hexadiyn-1,6-diol-bis-p-toluene sulfonate 2,4-hexadiyn-1,6-diol-bis-(p-chlorobenzene sulfonate)

Both the range of color change and the composition reactivity can be varied by codeposition of different acetylenic compounds (at least one of which contains at least two conjugated acetylene groups) or by the codeposition of one or more acetylenic compounds which contain at least two conjugated acetylene groups with one or more compounds which have similar molecular shape and polarity as the acetylenic compound, but which do not contain reactive acetylenic functionalities. Such codepositions can be from the vapor, melt or solution phases.

The thermal reactivity of acetylenic compounds of the invention can be increased by adding a suitable conventional polymerization enhancer. Examples of conventional enhancers include, but are not limited to, alkyl peroxides such as dicumyl peroxide, azo compounds such 2-t-butylazo-2-cyano propane, diacyl peroxides such as benzoyl peroxide, hydroperoxides such as cumene hydro peroxide, ketone peroxides such as cyclohexanone peroxide and peroxyesters such as t-butyl peroxyacetate. The thermal reactivity can be decreased by adding a suitable conventional polymerization inhibitor. Examples of polymerization inhibitors include, but are not limited to, quinones such as benzoquinone, and aromatic nitro-compounds such as m-nitrobenzene and 2,4-dinitrochlorobenzene.

In some cases, the acetylenic compounds are sensitive to exposure to short wavelength UV or UV-visible radiation. To construct a recording material from such compounds, it may be desirable to incorporate a filter material with the indicator to eliminate undesirable photo-induced reactions. The UV reactivity evident for certain acetylenic compounds is substantially eliminated by protecting such compounds from exposure with a UV-absorbing film over the acetylenic compound. Conventional UV stabilizers are also useful for this purpose. Examples of UV stabilizers include benzophenones such as 2-hydroxy-4-methoxy benzophenone, benzotrazoles such as 2-(2'hydroxy-5'-methylphenyl) benzotriazole, substituted acrylates such as ethyl-2-cyano-3,3-diphenyl acrylate and aryl esters such as phenyl salicylate.

In order to obtain the widest possible range of indicator response in one recording material, the recording material can contain a mixture of different indicator compounds, each of which undergoes a series of color changes during thermal history development. Alternatively, the recording material can consist of adjacent strips containing different acetylenic compositions with different activities.

In particular instances, it may be convenient to apply the indicator composition in the form of a printed message on the recording material, which will not be readable on the chosen background until the color development corresponding to a specified thermal treatment is obtained. Alternatively, a layer of the indicator compound on the recording material can be activated in the form of a printed message.

Preparation of Indicator Compounds

As described in U.S. Pat. Nos. 4,228,126 and 4,298,348, inactive forms of diacetylenes can generally be prepared by solvent recrystallization. In general, the inactive form of a diacetylene will be obtained from solution when very rapid precipitation conditions are employed. Typically, rapid precipitation will occur with rapid cooling of the solution, rapid evaporation of the solvent, or the addition of the solution to another liquid which is miscible with the solvent but acts as a non-solvent for the acetylenic compound.

The inactive form of a diacetylene can also be prepared by precipitating the inactive form of the compound from a solution at a rate sufficiently greater than the rate of precipitation of an active form of the compound, whereby substantially all of the precipitate obtained is the inactive form. In general, a solvent or a combination of solvents, is chosen such that the diacetylene recrystallizes rapidly from the solvent material. For example, the inactive form of 9-(N-carbazolyl)-5,7-nonadiyn-1-ol phenylurethane (PUCNDO), is obtained when recrystallizing crude material from acetone and allowing the crystallization to occur rapidly; the active form results when the recrystallization is allowed to proceed slowly.

The crystalline inactive form of the cyclic diacetylene, o,o'diacetylenyldiphenyl glutarate (DADPG), is obtained by rapid cooling of a (10:90) acetone/petroleum ether (b.p. 60°–110° C.) solution, at a concentration of 0.007 g/ml at room temperature, with an ice-water bath. The inactive form of DADPG is not solid state polymerizable with gamma-radiation. Alternately, the active form of DADPG is obtained by slow solvent evaporation of a 10:90 acetone/petroleum ether solution, at the same concentration, at room temperature. The active form is polymerizable upon exposure to gamma radiation. The crystalline inactive form melts at 133°–134° C., about 10° C. lower than the active form.

The inactive form of a diacetylene can be converted to the active form by heating the inactive form above its melting point, typically from about 1° C. to 20° C. above the melting point, and cooling the melt to room temperature. For example, the inactive form (colorless needles) of DADPG is heated to 150° C., about 16° C. to 17° C. above the melting point, and rapidly cooled to 25° C., resulting in an active form as red solids. By heating the inactive form of the indicator compounds at a temperature up to about 20° C. above its melting point, preferably from about 5° C. to about 15° C. above its melting point and then allowing the indicator compound to cool to room temperature (25° C.), the active form will generally be obtained.

The inactive form can also be prepared by spraying a solution of a diacetylene onto a substrate and allowing the solvent to evaporate rapidly. For example, spraying an acetone or tetrahydrofuran solution of 2,4-hexadiyn-1,6-diol bis(phenylurethane) (HDDPU) onto a substrate, and allowing the solvent to evaporate rapidly, for example, by passing a stream of air over the surface, results in the inactive form.

Recording Material

A recording material, as used herein, refers to any substrate that is suitable for use in a thermal imaging apparatus and that contains at least one inactive indicator compound which may be activated using a thermal imaging apparatus incorporated therein such as in a base sheet or a coating on a base sheet. The recording material may take the form of an article of product packaging such as a cardboard container or a label that can be readily affixed to a product before or after activation of the indicator compound.

The substrate can be any material that does not chemically interfere with the active or inactive forms of the indicator compound and that provides sufficient rigid support for the inactive form of the indicator compound contained within or deposited upon the substrate. The back of the substrate, in addition, may also be coated with an adhesive to secure the substrate to the article being monitored.

Substrates that may be used as part of the recording material in conjunction with this invention may include all types of paper or adhesive labels, including both thermal paper or non-thermal paper, or any combination thereof. Thermal paper that may be used in accordance with this invention are described, for example, in U.S. Pat. No. 3,080,254, U.S. Pat. No. 3,241,997, U.S. Pat. No. 3,795,532, U.S. Pat. No. 3,094,417, U.S. Pat. No. 4,082,901 and in the *Handbook of Imaging Materials*, 1991, ed. by Arthur S. Diamond (Marcel Dekker, New York).

Thermal paper will contain thermal reactive dyes, such as azo or leuco dyes used with a developer. Leuco dyes are colorless or light colored basic substances which become colored when oxidized by acidic substances (developers). The dye and developer are preferably solid at ambient temperature and have a melting point below the operating temperature of a thermal print head of a thermal imaging apparatus.

Examples of leuco dyes that can be used herein are described as follows:

(a) leuco bases of triphenylmethane dyes such as 3,3-bis(p-dimethylaminophenyl)-phthalide, 3,3-bis(p-dimethylaminophenyl)-6-dimethylaminophthalide (Crystal Violet Lactone), 3,3-bis(p-dimethylaminophenyl)-6-diethylaminophthalide, 3,3-bis(p-dimethylaminophenyl)-6-chlorophthalide, and 3,3-bis(p-dibutylaminophenyl)-phthalide;

(b) leuco bases of fluoran dyes such as 3-cyclohexylamino-6-chlorofluoran, 3-(N-N-diethylamino)-5-methyl-7-(N,N-Dibenzylamino) fluoran, 3-dimethylamino-5,7-dimethylfluoran and 3-diethylamino-7-methylfluoran;

(c) miscellaneous fluoran dyes such as 3-diethylamino-6-methyl-7-chlorofluoran, 3-pyrrolidino-6-methyl-7-anilinofluoran, and 2-[3,6-bis(diethylamino)-9-(0-chloroanilino)xanthybenzoic acid lactam]; and (d) lactone compounds such as 3-(2'-hydroxy-4'-dimethylaminophenyl)-3-(2'[-methoxy-5'-chlorophenyl)phthalide, 3-(2'-hydroxy-4'-dimethylaminophenyl)-3-(2'methoxy-5'-nitrophenyl-phthalide, 3-(2'-hydroxy-4'-diethylaminophenyl)-3-(2'methoxy-5-methylphenyl)phthalide, and 3-(2'-methoxy-4'-dietnethylaminophenyl)-3-(2'-hydroxy-4'-chloro-5'-methylphenyl)-phthalide.

Examples of suitable developers are phenol compounds, organic acids or metal salts thereof and hydroxybenzoic acid esters Examples of phenol compounds include 4,4'-isopropylene-diphenol (bisphenol A), p-tert-butylphenol, 2-4-dinitrophenol, 3,4-dichlorophenol, p-phenylphenol, 4,4-cyclohexylidenediphenol. Useful examples of organic acid and metal salts thereof include 3-tert-butylsalicylic acid, 3,5-tert-butysalicylic acid, 5-a-methylbenzylsalicylic acid and salts thereof of zinc, lead, aluminum, magnesium or nickel.

Sensitizers or thermosensitivity promoter agents are used in the recording materials of the present invention to give a good color density to the images obtained. Some of the common sensitizers which are suitable are fatty acid amide compounds such as acetamide, stearic acid amide, linolenic acid amide, lauric acid amide, myristic acid amide, methylol compounds or the above mentioned fatty acid amides such as methylenebis (stearamide), and ethylenebis (stearamide), and compounds of p-hydroxybenzoic acid esters such as methyl p-hydroxybenzoate, n-propyl p-hydroxybenzoate, isopropyl p-hydroxybenzoate, benzyl p-hydroxybenzoate.

In the preparation of the thermal paper according to this invention, a suitable base sheet is first chosen as it's optical and mechanical properties significantly affect the final properties of the thermal paper. The active compounds (dye, developer and sensitizer) are then coated on this base sheet with or without the indicator compound. In selecting the dye, developer, sensitizer and indicator compound, consideration should be given to the operating temperature of the printer head to be used.

If thermal paper is employed, a thermal image may be generated on the paper in conjunction with activation of the indicator compound in the recording material. The indicator compounds may be incorporated into the recording material including thermal paper or non-thermal paper or labels, by a variety of methods that are well known in the art. Alternatively the indicator compounds may be applied to the surface of the paper or labels. The application of the indicator compounds to the recording material will vary depending on the mechanism of activation of the indicator compounds. If the indicator compounds are activated by melt recrystallization, they may, for example, be applied to the surface of the substrate. However, if the indicator compounds are activated by combining two different indicator compounds, the different indicator compounds may, for example be localized in different layers within the recording material. As an additional example, two different indicator compounds may be present in encapsulated form within the recording material, wherein the compounds are able to mix and polymerize only after the application of heat has released the encapsulated forms.

Printers

A direct thermal imaging apparatus as used herein refers to any apparatus which is suitable for the application of thermal energy to the recording material to activate indicator compounds in the recording material. A survey of direct thermal imaging methods is given, for example, in *Imaging Systems*, 1976, Kurt I. Jacobson and Ralph E. Jacobson (The Focal Press, London and New York), in Chapter VII, Subsection 7.1 on Thermography. Direct thermal printing is also generally described in the *Handbook of imaging Materials*, 1991, ed. by Arthur S. Diamond (Marcel Dekker, New York).

Use of Indicator Compounds

Particular indicator compounds may be matched to a particular perishable product or to another particular use. For example, the indicator compounds may be selected to parallel the response of a particular product to changes in temperature over time. Examples of perishable products for which the use of thermal printer activated indicator compounds may be useful include, for example, packaged fresh and frozen foods, dairy products, meat, pharmaceuticals, photographic film, canned goods, spices, vitamins, seeds, plants. Other products which slowly degrade over time and for which time-temperature indicators may be useful include, for example, paints, coatings, adhesives, caulks etc. Time-temperature indicators could also be useful as sterilization indicators or as cooking indicators to indicate when a product is sterilized or finished cooking.

Processes monitored by indicator compounds may include undesirable processes such as, for example, degradation or spoilage of products or desirable processes such as, for example, ripening of produce.

BRIEF DESCRIPTION OF THE DRAWING

FIGS. 1A–1D illustrate the aging sequence of a time-temperature indicator of this invention.

FIG. 1A is a time temperature indicator (10) immediately after activation of the indicator compound by processing recording material (20) in a thermal imaging apparatus. Central portion (1) of time temperature indicator (10) contains the indicator compounds and is initially light colored as compared to the color of the outer ring (2), which is the reference color.

FIG. 1B illustrates TTI (10) of FIG. 1A sometime after activation in a thermal imaging apparatus. Central portion (1) has darkened with time and temperature but is still lighter than the outer ring (2), indicating that the labeled product is still usable.

FIG. 1C shows TTI (10) of FIG. 1A with no discernable central portion or outer ring in that they are the same color. The product is still usable but must be used immediately.

FIG. 1D illustrates TTI (10) of FIG. 1A where usability of the product can not be guaranteed. Central portion (1) is darker than the outer ring (2).

The colored outer ring (2) may be generated with the thermal imaging apparatus at the same time as activation of the indicator compounds.

Without further elaboration, it is believed that one skilled in the art, using the preceding description, can utilize the present invention to its fullest extent. The preceding preferred specific embodiments are, therefore, to be construed as merely illustrative, and not limitative of the remainder of the disclosure in any way whatsoever.

The entire disclosure of all patent applications, patents, and publications cited herein are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A recording material comprising a base sheet suitable for feeding into a thermal printer, wherein said thermal printer is suitable for generating a thermal image on thermal paper, wherein said recording material has at least one time-temperature indicator (TTI) compound coated on said base sheet or incorporated in said base sheet, wherein the indicator compound is coated on the surface of said base sheet or incorporated in the surface of said base sheet so as to be convertible from an inactive state to an active state when heat is applied by said thermal printer wherein the indicator compound exhibits detectable changes in response to an exposure element when in an active state, and wherein the indicator compound is coated on the base sheet or incorporated in the base sheet in a concentration which permits the recording material to function as a time-temperature indicator when said indicator compound is active, and wherein the indicator compound is convertible from an inactive state to an active state in said thermal printer operating at a temperature in the range of 50° C. to 250° C.

2. A recording material according to claim 1, wherein at least one indicator compound is an acetylene compound.

3. A recording material according to claim 2, wherein at least one acetylene compound is selected from the group consisting of 2,4-hexadiyn-1,6-diol bis(phenylurethane); 2,4-hexadiyn-1,6-diol bis(p-methoxybenzene sulfonate); 9-(N-carbazolyl)-5,7-nonadiyn-1-ol phenylurethane; o,o'-diacetylenyldiphenyl glutarate; 2,4-hexadiyn-1,6-diol-bis-p-toluene sulfonate; 2,4-hexadiyn-1,6-diol-bis-(t-phenylazophenyl sulfonate); 2,4-hexadiyn-1,6-bis-(p-toluene sulfonate); and 2,4-hexadiyn-1,6-diol-bis-(p-chlorobenzene sulfonate).

4. A recording material according to claim 2, wherein the recording material also contains a component that is a polymerization enhancer or a polymerization inhibitor for at least one indicator compound.

5. A recording material according to claim 2, wherein at least one acetylene compound has two conjugated acetylene groups.

6. A recording material according to claim 1, wherein the indicator compound is convertible from an inactive state to an active state by melt recrystallization.

7. A recording material according to claim 1, which additionally comprises an initiator compound and wherein the indicator compound is convertible from a substantially inactive state to an active state by activation of said initiator compound.

8. A recording material according to claim 1, wherein the indicator compound exhibits detectable changes in color in response to integrated time-temperature exposure when in an active state.

9. A recording material according to claim 8, wherein the indicator compound exhibits detectable changes color in response to temperatures of 0° C. and above.

10. A recording material according to claim 8, wherein the indicator compound exhibits detectable changes color in response to temperatures of 0° C. and below.

11. A recording material according to claim 1, wherein the indicator compound exhibits detectable changes color in response to actinic radiation.

12. A recording material according to claim 1, wherein the indicator compound exhibits detectable changes in color in response to visible light, actinic radiation with a wavelength in the UV range, actinic radiation with a wavelength in the x-ray range or a combination thereof.

13. A recording material as in claim 1, wherein the heat applied by a thermal printer to convert the indicator compound from an inactive to an active state is applied in less than one thousandth of a minute.

14. A recording material comprising a base sheet suitable for feeding into a thermal printer that is suitable for generating a thermal image on a thermal paper having at least one time-temperature indicator (TTI) compound coated on said base sheet or incorporated in said base sheet wherein the indicator compound is coated on the surface of said base sheet or incorporated in the surface of said base sheet so as to be convertible from an inactive state to an active state when heat is applied by said thermal printer wherein the indicator compound exhibits detectable changes in response to an exposure element when in an active state, and wherein the indicator compound is coated on the base sheet or incorporated in the base sheet in a concentration which permits the recording material to function as a time-temperature indicator when said indicator compound is active wherein the recording material also contains dye components for thermal printing by said thermal printer.

15. A method which comprises:
providing a recording material suitable for use in a thermal printer, wherein said thermal printer is suitable for generating a thermal image on a thermal paper,
wherein said recording material has at least one indicator compound incorporated therein,
wherein the indicator compound is convertible from an inactive state to an active state when heat is applied thereto within said thermal printer and
said indicator compound provides detectable changes in color in response to an exposure element when in an active state; and
heating the recording material in said thermal printer to convert at least some of the indicator compound from an inactive state to an active state and form a time-temperature indicator,
wherein said thermal printer is operated at a temperature in the range of 50° C. to 250° C.

16. A method according to claim 15, wherein at least one indicator compound is an acetylene compound.

17. A method according to claim 16, wherein at least one acetylene compound has two conjugated acetylene groups.

18. A method according to claim 16, wherein at least one acetylene compound is selected from the group consisting of 2,4-hexadiyn-1,6-diol bis(phenylurethane); 2,4-hexadiyn-1,6-diol bis(p-methoxybenzene sulfonate); 9-(N-carbazolyl)-5,7-nonadiyn-1-ol phenylurethane; o,o'-diacetylenyldiphenyl glutarate; 2,4-hexadiyn-1,6-diol-bis-p-toluene sulfonate; 2,4-hexadiyn-1,6-diol-bis-(t-phenylazophenyl sulfonate); 2,4-hexadiyn-1,6-bis-(p-toluene sulfonate); and 2,4-hexadiyn-1,6-diol-bis-(p-chlorobenzene sulfonate).

19. A method according to claim 15, wherein the indicator compound is converted from an inactive state to an active state by melt recrystallization and heating the recording medium in the thermal printer melts the indicator compound.

20. A method according to claim 15, wherein the indicator compound is converted from an inactive state to an active state by an initiator compound and heating the recording material in the thermal printer activates the initiator compound.

21. A method according to claim 15, wherein the recording material also contains dye components for thermal printing by the thermal printer and heating the recording material in the thermal printer activates these dye components to form the thermal image.

22. A method according to claim 15, wherein the time-temperature indicator formed is sensitive to integrated time-temperature exposure after activation.

23. A method according to claim 22, wherein the time-temperature indicator formed is sensitive to temperatures of 0° C. and above.

24. A method according to claim 22, wherein the time-temperature indicator formed is sensitive to temperatures of 0° C. and below.

25. A method according to claim 15, wherein the time-temperature indicator formed is sensitive to actinic radiation after activation.

26. A method according to claim 15, wherein the time-temperature indicator formed is sensitive to visible light, actinic radiation with a wavelength in the UV range, actinic radiation with a wavelength in the X-ray range or a combination thereof.

* * * * *